(12) United States Patent
Suzuki et al.

(10) Patent No.: US 9,952,101 B2
(45) Date of Patent: Apr. 24, 2018

(54) SPECTROMETRY DEVICE AND SPECTROMETRY METHOD

(71) Applicant: HAMAMATSU PHOTONICS K.K., Hamamatsu-shi, Shizuoka (JP)

(72) Inventors: Kengo Suzuki, Hamamatsu (JP); Kazuya Iguchi, Hamamatsu (JP)

(73) Assignee: HAMAMATSU PHOTONICS K.K., Hamamatsu-shi, Shizuoka (JP)

(*) Notice: Subject to any disclaimer, the term of this patent is extended or adjusted under 35 U.S.C. 154(b) by 0 days.

(21) Appl. No.: 15/531,772

(22) PCT Filed: Nov. 19, 2015

(86) PCT No.: PCT/JP2015/082576
§ 371 (c)(1),
(2) Date: May 31, 2017

(87) PCT Pub. No.: WO2016/088568
PCT Pub. Date: Jun. 9, 2016

(65) Prior Publication Data
US 2017/0261375 A1 Sep. 14, 2017

(30) Foreign Application Priority Data
Dec. 2, 2014 (JP) ................................. 2014-243641

(51) Int. Cl.
*G01N 21/64* (2006.01)
*G01J 3/36* (2006.01)

(52) U.S. Cl.
CPC ............. *G01J 3/36* (2013.01); *G01N 21/64* (2013.01); *G01N 2021/6421* (2013.01)

(58) Field of Classification Search
CPC ..... G01J 3/36; G01N 21/64; G01N 2021/6421
See application file for complete search history.

(56) References Cited

U.S. PATENT DOCUMENTS

2002/0024664 A1* 2/2002 Yokota .................. G01J 1/04
356/319

FOREIGN PATENT DOCUMENTS

| CN | 1890555 | 0/2007 |
|---|---|---|
| CN | 1587931 | 3/2005 |

(Continued)

OTHER PUBLICATIONS

International Preliminary Report on Patentability dated Jun. 15, 2017 for PCT/JP2015/082576.

*Primary Examiner* — Mark R Gaworecki
(74) *Attorney, Agent, or Firm* — Drinker Biddle & Reath LLP

(57) ABSTRACT

A spectroscopic measurement apparatus includes a light source, an integrator, a first spectroscopic detector, a second spectroscopic detector, and an analysis unit. The integrator includes an internal space in which a measurement object is disposed, a light input portion for inputting light to the internal space, a light output portion for outputting light from the internal space, and a sample attachment portion for attaching the measurement object. The first spectroscopic detector receives the light output from the integrator, disperses the light of a first wavelength region, and acquires first spectrum data. The second spectroscopic detector receives the light output from the integrator, disperses the light of a second wavelength region, and acquires second spectrum data. The first wavelength region and the second wavelength region include a wavelength region partially overlapping each other.

14 Claims, 12 Drawing Sheets

(56) References Cited

FOREIGN PATENT DOCUMENTS

| | | |
|---|---|---|
| CN | 101329411 | 12/2008 |
| CN | 102243102 | 11/2011 |
| JP | 2002-62189 A | 2/2002 |
| JP | 2004-257835 A | 9/2004 |
| JP | 2005-192610 A | 7/2005 |
| JP | 2011-196735 A | 10/2011 |
| JP | 2015-210217 A | 11/2015 |

* cited by examiner

SPECTROMETRY DEVICE AND SPECTROMETRY METHOD

TECHNICAL FIELD

An aspect of the present invention relates to a spectroscopic measurement apparatus and a spectroscopic measurement method.

BACKGROUND ART

Spectroscopic measurement techniques for measuring light emission efficiency and the like of a measurement object with an integrator and a spectroscopic detector have been known. The integrator includes an internal space in which the measurement object is disposed, a light input portion for inputting the light output from a light source into the internal space, and a light output portion for outputting the measurement target light from the internal space to the outside. The internal space of the integrator is, for example, spherical, and covered with an inner wall surface having high reflectance and excellent diffuseness. Alternatively, the internal space of the integrator is, for example, hemispherical, and in this case, an inner wall of a hemispherical portion has a wall surface with high reflectance and excellent diffuseness and a planar portion is a flat mirror with high reflectance (see Patent Document 1).

In the integrator, excitation light output from the light source can be input from the light input portion into the internal space, and the excitation light can be diffused and reflected multiple times in the internal space. In addition, in the integrator, emission light (such as fluorescence), generated when the measurement object disposed in the internal space is irradiated with the excitation light, can also be diffused and reflected multiple times in the internal space. Then, the integrator outputs the measurement target light from the internal space to the outside through the light output portion. The measurement target light is the excitation light and/or the emission light.

The spectroscopic detector disperses the measurement target light output from the integrator to the outside, and acquires spectrum data. The spectroscopic detector disperses the measurement target light into respective wavelength components through a spectroscopic element such as a grating or a prism, and detects the intensity of the dispersed light of each wavelength using an optical sensor. The optical sensor has a plurality of light receiving portions arrayed one-dimensionally, and by detecting the light intensity of the wavelength component by the light receiving portion corresponding to each wavelength, the spectrum data of the measurement target light can be acquired. Then, by analyzing the spectrum data, the luminous efficiency and the like of the measurement object can be measured without depending on the angle characteristic and the like of the light emission of the measurement object.

In the spectroscopic measurement technique using the integrator, the measurement object may be the organic EL (electroluminescence) material or the fluorescent material. The measurement object may be in the arbitrary form, such as a solution, a thin film, or powder. For such a measurement object, evaluation of the photoluminescence quantum yield (internal quantum efficiency) is important. The photoluminescence quantum yield refers to the ratio of the number of photons of the emission light generated in the measurement object to the number of photons of the excitation light absorbed by the measurement object. The spectroscopic measurement technique using the integrator is preferably applicable for evaluating the photoluminescence quantum yield of the measurement object.

CITATION LIST

Patent Literature

Patent Document 1: Japanese Patent Application Laid-Open No. 2011-196735

SUMMARY OF INVENTION

Technical Problem

An apparatus that can perform spectroscopic measurement of the measurement target light in a wavelength region of 200 to 950 nm, a wavelength region of 350 to 1100 nm, or a wavelength region of 900 to 1650 nm has been commercially available as the spectroscopic measurement apparatus using the integrator.

However, some measurement objects have the excitation light wavelength in a short-wavelength region of 400 to 600 nm and have the fluorescence wavelength in a long-wavelength region of 1100 nm or more. The conventional spectroscopic measurement apparatuses have failed to perform spectroscopic measurement in a wavelength region of 400 to 600 nm and a wavelength region of 1100 nm or more at the same time, and therefore, cannot perform spectroscopic measurement of the measurement target light in the wider wavelength region, and thus cannot measure the luminous efficiency and the like of such a measurement object.

Patent Document 1 describes in paragraph 0037 that "the measurement region of the measuring device 70 is set so as to cover both the wavelength region of the excitation light emitted from the light source device 60 and the wavelength region of the fluorescence generated in the sample SMP by receiving the excitation light". However, Patent Document 1 does not describe how to acquire the spectrum data of the measurement target light when the measurement target light including both the excitation light and the fluorescence has the wide band.

One aspect of the present invention has been made in order to solve the above problem, and an object thereof is to provide a spectroscopic measurement apparatus and a spectroscopic measurement method that can perform spectroscopic measurement of measurement target light in a wider wavelength region.

Solution to Problem

A spectroscopic measurement apparatus according to one aspect of the present invention includes (1) an integrator including an internal space in which a measurement object is disposed, a light input portion for inputting light from outside to the internal space, and a light output portion for outputting light from the internal space to the outside; (2) a first spectroscopic detector for dispersing light of a first wavelength region in the light output from the light output portion and acquiring first spectrum data for a first exposure time; (3) a second spectroscopic detector for dispersing light of a second wavelength region partially overlapping with the first wavelength region in the light output from the light output portion and acquiring second spectrum data for a second exposure time; and (4) an analysis unit for analyzing the first spectrum data and the second spectrum data on the basis of the first exposure time and the second exposure time.

A spectroscopic measurement method according to one aspect of the present invention is a method (1) for performing spectroscopic measurement using an integrator including an internal space in which a measurement object is disposed, a light input portion for inputting light from outside to the internal space, and a light output portion for outputting light from the internal space to the outside, and the method includes (2) inputting light from the light input portion of the integrator to the internal space; (3) dispersing light of a first wavelength region in the light output from the light output portion and acquiring first spectrum data for a first exposure time by a first spectroscopic detector; (4) dispersing light of a second wavelength region partially overlapping with the first wavelength region in the light output from the light output portion and acquiring second spectrum data for a second exposure time by a second spectroscopic detector; and (5) analyzing the first spectrum data and the second spectrum data on the basis of the first exposure time and the second exposure time by an analysis unit.

Advantageous Effects of Invention

According to one aspect of the present invention, spectroscopic measurement can be performed for the measurement target light in the wider wavelength region. For example, the luminous efficiency of the measurement object whose excitation light wavelength is in a visible region and whose fluorescence wavelength is in a near-infrared region of wavelength 1100 nm or more can be evaluated.

DESCRIPTION OF EMBODIMENTS

Hereinafter, embodiments for carrying out the present invention will be described in detail with reference to the accompanying drawings. In the description of the drawings, the same elements will be denoted by the same reference signs, without redundant description. The present invention is not limited to these examples, and it is intended that the present invention includes all the changes within an equivalent meaning and range to the claims indicated in the claims.

Figure 1:
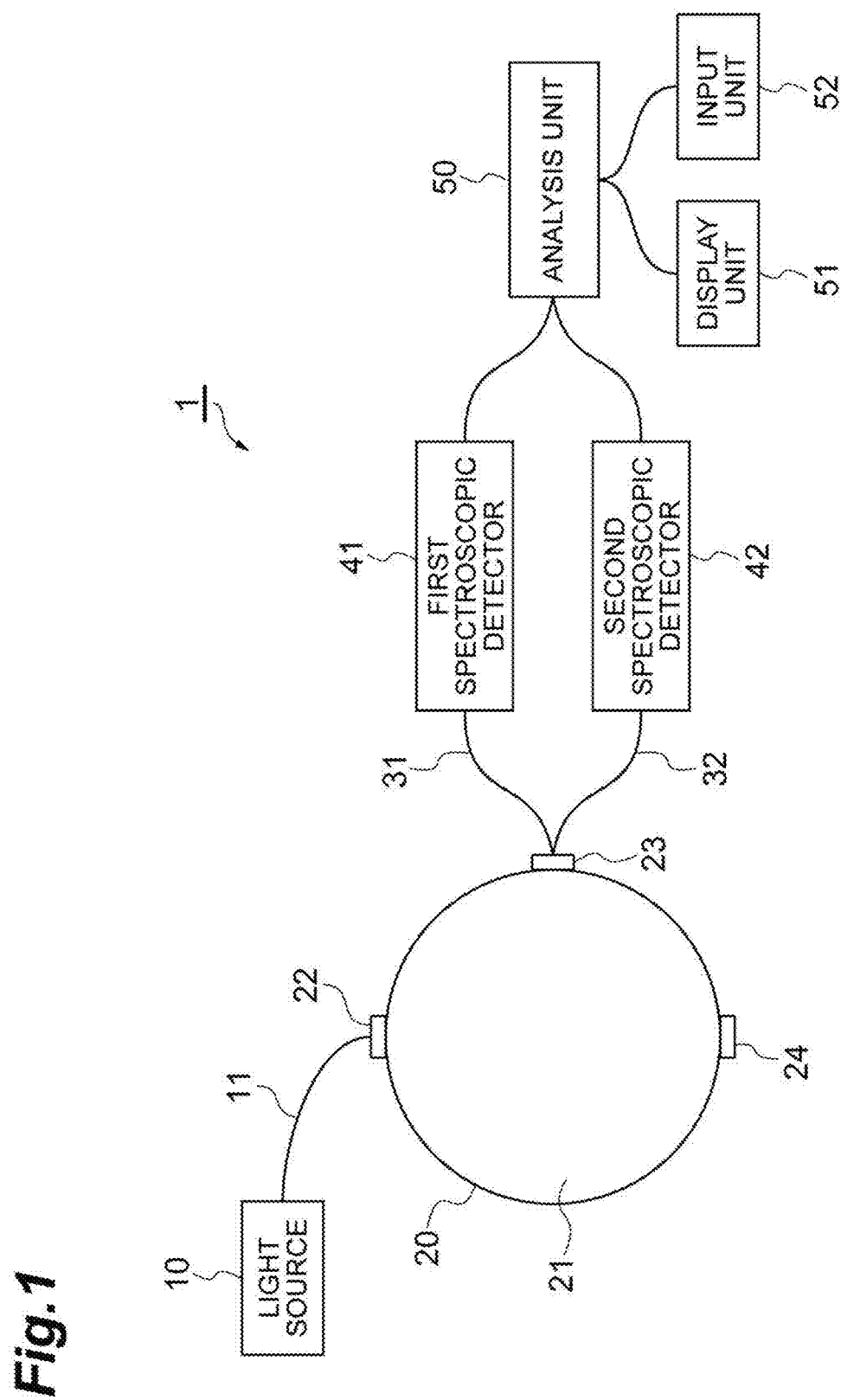
FIG. 1 is a diagram illustrating a configuration of a spectroscopic measurement apparatus 1.

FIG. 1 is a diagram illustrating a configuration of a spectroscopic measurement apparatus 1. The spectroscopic measurement apparatus 1 includes a light source 10, an input light guide 11, an integrator 20, a first output light guide 31, a second output light guide 32, a first spectroscopic detector 41, a second spectroscopic detector 42, an analysis unit 50, a display unit 51, and an input unit 52.

The light source 10 outputs light to be input to an internal space 21 of the integrator 20. The light output from the light source 10 includes, for example, standard light having a known spectrum for calibrating the sensitivity of the entire apparatus, reference light for correcting the spectrum data acquired by the first spectroscopic detector 41 and the second spectroscopic detector 42, and excitation light with which the measurement object disposed in the internal space 21 of the integrator 20 is irradiated. The wavelength of the light output from the light source 10 may be variable, and is preferably variable in the wavelength range of, for example, 250 nm to 1600 run. Further, the light source 10 may include an ND filter or a relay optical system. The input light guide 11 guides the light output from the light source 10 to a light input portion 22 of the integrator 20.

The integrator (optical integrator) 20 includes the internal space 21 in which the measurement object is optically disposed, the light input portion 22 for inputting the light (input light) output from the light source 10 and guided by the input light guide 11 into the internal space 21, a light output portion 23 for outputting the light (output light) from the internal space 21 to the outside, and a sample attachment portion 24 for attaching the measurement object. The internal space 21 is spherical and is covered with an inner wall surface having high reflectance and excellent diffuseness. The sample attachment portion 24 disposes the measurement object at a position where the light input to the internal space 21 through the light input portion 22 is incident.

In the integrator 20, the light output from the light source 10 can be input into the internal space 21 through the light input portion 22 and the light can be diffused and reflected multiple times in the internal space 21. Further, in the integrator 20, the emission light generated in the measurement object disposed in the internal space 21 (for example, fluorescence) can also be diffused and reflected multiple times in the internal space 21. Then, the integrator 20 outputs the measurement target light from the internal space 21 to the outside through the light output portion 23. The measurement target light is the light input from the light source 10 to the internal space 21 and/or the emission light generated in the measurement object.

To the sample attachment portion 24, for example, a sample container for holding the measurement object that outputs up-conversion light by input of the excitation light is attached. For example, when the measurement object is liquid, a solution sample cell including a transparent material that transmits light (for example, quartz glass or plastic) is attached to the sample attachment portion 24 as the sample container. When the measurement object is solid like powder or a thin film, a solid sample cell or a solid sample container including a transparent material that transmits light (for example, quartz glass or plastic) or metal is attached to the sample attachment portion 24 as the sample container.

Here, the measurement object may be disposed entirely within the internal space 21 of the integrator 20, or a part of the measurement object may be disposed in the internal space 21 of the integrator 20. Using an optical attachment attached to the sample attachment portion 24, the sample disposed outside the inner wall of the integrator 20 may be optically disposed in the internal space 21 of the integrator 20.

The first output light guide 31 guides the light output from the light output portion 23 of the integrator 20 to the first spectroscopic detector 41. The second output light guide 32 guides the light output from the light output portion 23 of the integrator 20 to the second spectroscopic detector 42. The first output light guide 31 and the second output light guide 32 may be bundled into one on the light output portion 23 side.

The first spectroscopic detector 41 receives the light output from the light output portion 23 of the integrator 20 and guided by the first output light guide 31, disperses the light of a first wavelength region in the received light, and acquires first spectrum data. The second spectroscopic detector 42 receives the light output from the light output portion 23 of the integrator 20 and guided by the second output light guide 32, disperses the light of a second wavelength region in the received light, and acquires second spectrum data. The first wavelength region and the second wavelength region overlap partially in a wavelength region (hereinafter referred to as a "common wavelength region") and the first wavelength region is on the short-wavelength side compared to the second wavelength region.

Each of the spectroscopic detectors 41 and 42 disperses the input light into each wavelength component through a spectroscopic element such as a grating or a prism, and detects the intensity of the dispersed light with each wavelength using an optical sensor. The optical sensor has a plurality of light receiving portions arrayed one-dimensionally, and by detecting the light intensity of the wavelength component by the light receiving portion corresponding to each wavelength, the spectrum data of the measurement target light can be acquired. The spectroscopic element of the first spectroscopic detector 41 disperses the light in the first wavelength region and the optical sensor of the first spectroscopic detector 41 is sensitive to the light in the first wavelength region. The spectroscopic element of the second spectroscopic detector 42 disperses the light in the second wavelength. region and the optical sensor of the second spectroscopic detector 42 is sensitive to the light in the second wavelength region.

For example, the optical sensor of the first spectroscopic detector 41 is a CCD linear image sensor or a CMOS linear image sensor formed on a silicon substrate, and is sensitive to light of a wavelength of 350 nm to 1100 nm as the first wavelength region. Further, the optical sensor of the second spectroscopic detector 42 is an InGaAs linear image sensor, and is sensitive to light of a wavelength of 900 nm to 1650 nm as the second wavelength region. The first spectroscopic detector 41 and the second spectroscopic detector 42 may be different from each other in the sensitivity characteristic, wavelength resolution, or the like.

In each of the spectroscopic detectors 41 and 42, it is preferable that the measurement time (exposure time) can be variably set and that the exposure time is set appropriately in accordance with the sensitivity of the optical sensor. In the example of the above optical sensors, since the optical sensor sensitivity of the second spectroscopic detector 42 is lower than that of the first spectroscopic detector 41, it is preferable that the exposure time of the second spectroscopic detector 42 is set longer than that of the first spectroscopic detector 41.

To the analysis unit (analyzer) 50, the first spectrum data acquired by the first spectroscopic detector 41 is input, and further the second spectrum data acquired by the second spectroscopic detector 42 is input, and the analysis unit analyzes the first spectrum data and the second spectrum data. The analysis process will be described later. The analysis unit 50 includes a storage unit (storage) that stores the input first spectrum data and second spectrum data, the analysis results, and the like. The analysis unit 50 may control the light source 10, the first spectroscopic detector 41, and the second spectroscopic detector 42. The analysis unit 50 is a computer including a processor and a memory. The analysis unit 50 uses the processor to execute various analysis and controls. Such a computer corresponds to, for example, a personal computer or a tablet terminal. The analysis unit 50 can be integrated with the display unit 51 and the input unit 52.

The display unit (display) 51 displays the first spectrum data and the second spectrum data input by the analysis unit 50, and also displays the analysis results by the analysis unit 50. The input unit 52 corresponds to, for example, a keyboard or a mouse, accepts the input instruction from an operator who performs the spectroscopic measurement using the spectroscopic measurement apparatus 1, and sends the input information (for example, measurement condition or display condition) to the analysis unit 50.

Next, the operation of the spectroscopic measurement apparatus 1 according to the present embodiment and the spectroscopic measurement method according to the present embodiment will be described. In the spectroscopic measurement method of the present embodiment, spectroscopic measurement is performed using the spectroscopic measurement apparatus 1 described above. In the present embodiment, the first wavelength region in which the first spectroscopic detector 41 is sensitive and the second wavelength region in which the second spectroscopic detector 42 is sensitive overlap with each other partially in a wavelength region (common wavelength region), and by using this feature, the spectroscopic measurement is performed.

In the operation example to be described below, the excitation light output from the light source 10 is input from the light input portion 22 of the integrator 20 to the internal space 21, the measurement object disposed in the internal space 21 is irradiated with the excitation light to generate the fluorescence, and the measurement target light (excitation light and/or emission light) is output from the light output portion 23 of the integrator 20. Then, the output light in the first wavelength region including the excitation light is dispersed by the first spectroscopic detector 41 and the first spectrum data is acquired, and further, the output light in the second wavelength region including the fluorescence is dispersed by the second spectroscopic detector 42 and the second spectrum data is acquired.

Figure 2:
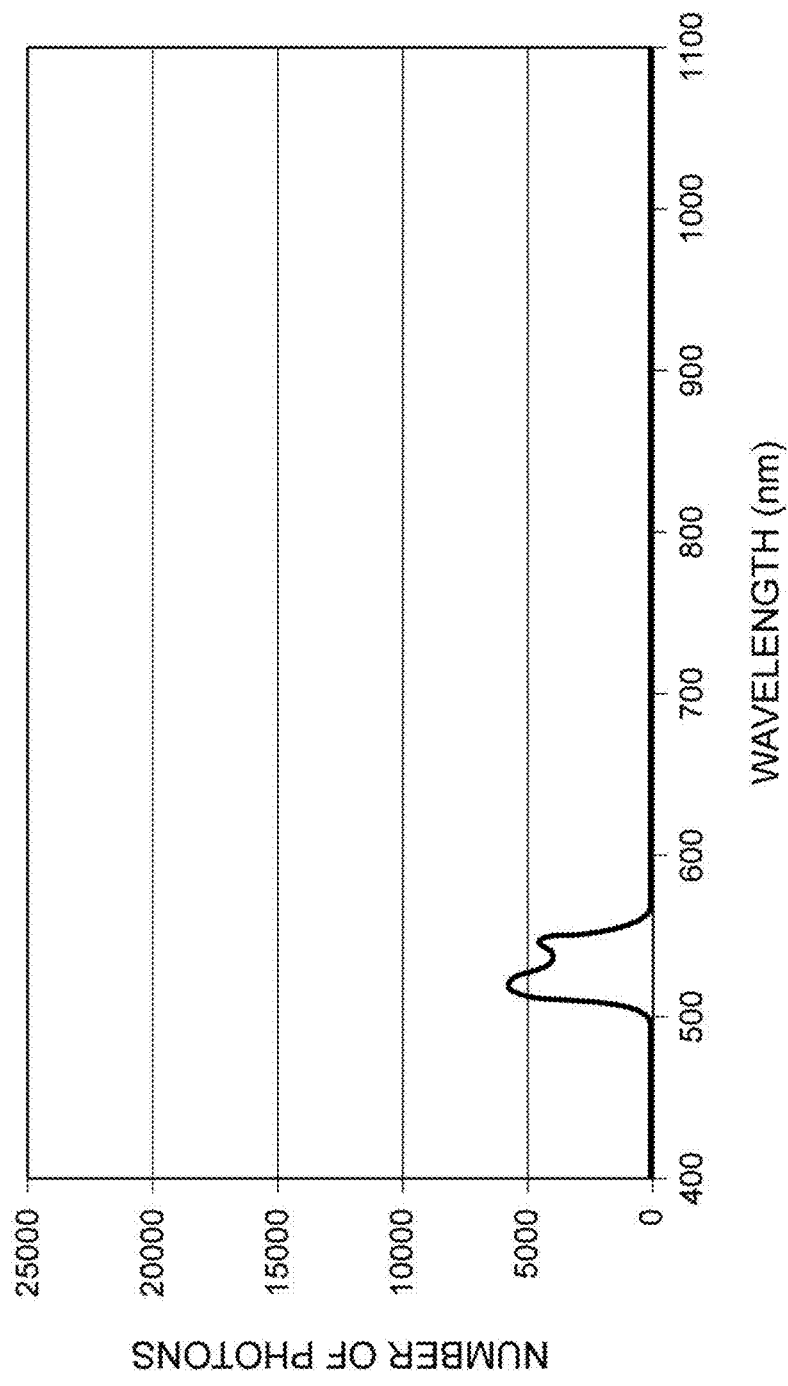
FIG. 2 is a diagram illustrating an example of a first spectrum in a first wavelength region including an excitation light wavelength of 530 mn.
Figure 3:
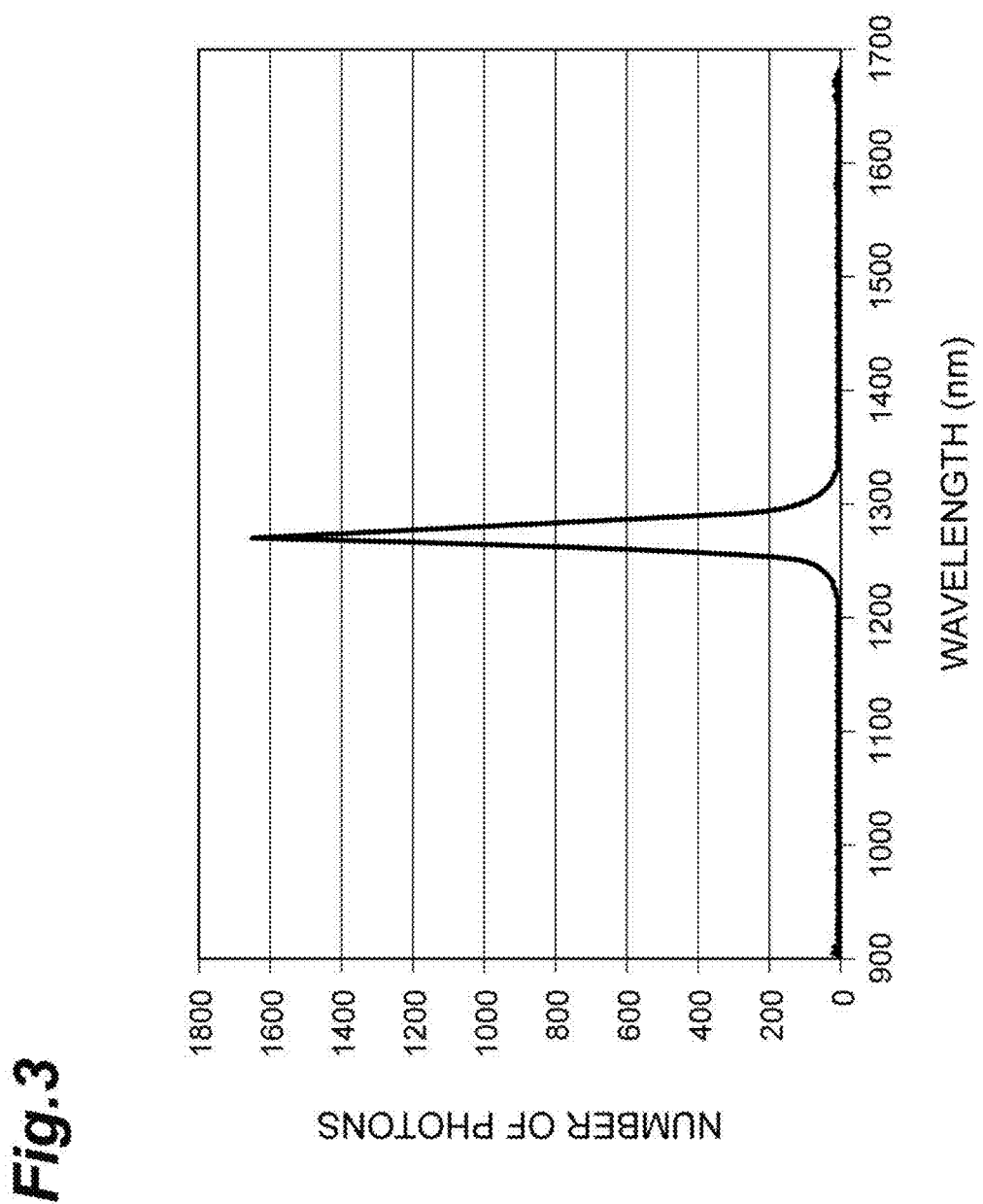
FIG. 3 is a diagram illustrating an example of a second spectrum in a second wavelength region including a fluorescence wavelength of 1270 nm.

The excitation light wavelength is 530 nm, and the first wavelength region is from 350 nm to 1100 nm. The fluorescence wavelength is 1270 nm, and the second wavelength region is from 900 nm to 1650 nm. The common wavelength region is from 900 nm to 1100 nm. FIG. 2 is a diagram illustrating an example of the first spectrum in the first wavelength region including the excitation light wavelength of 530 nm. FIG. 3 is a diagram illustrating an example of the second spectrum in the second wavelength region including the fluorescence wavelength of 1270 nm. In these figures, the vertical axis represents the number of photons (relative value). In general, the first spectroscopic detector 41 and the second spectroscopic detector 42 are different from each other in the sensitivity characteristic, the wavelength resolution, and the like, and therefore, the spectrum in the entire wavelength region cannot be obtained by simply connecting the first spectrum and the second spectrum, and accordingly, the photoluminescence quantum yield of the measurement object cannot be evaluated.

Figure 4:
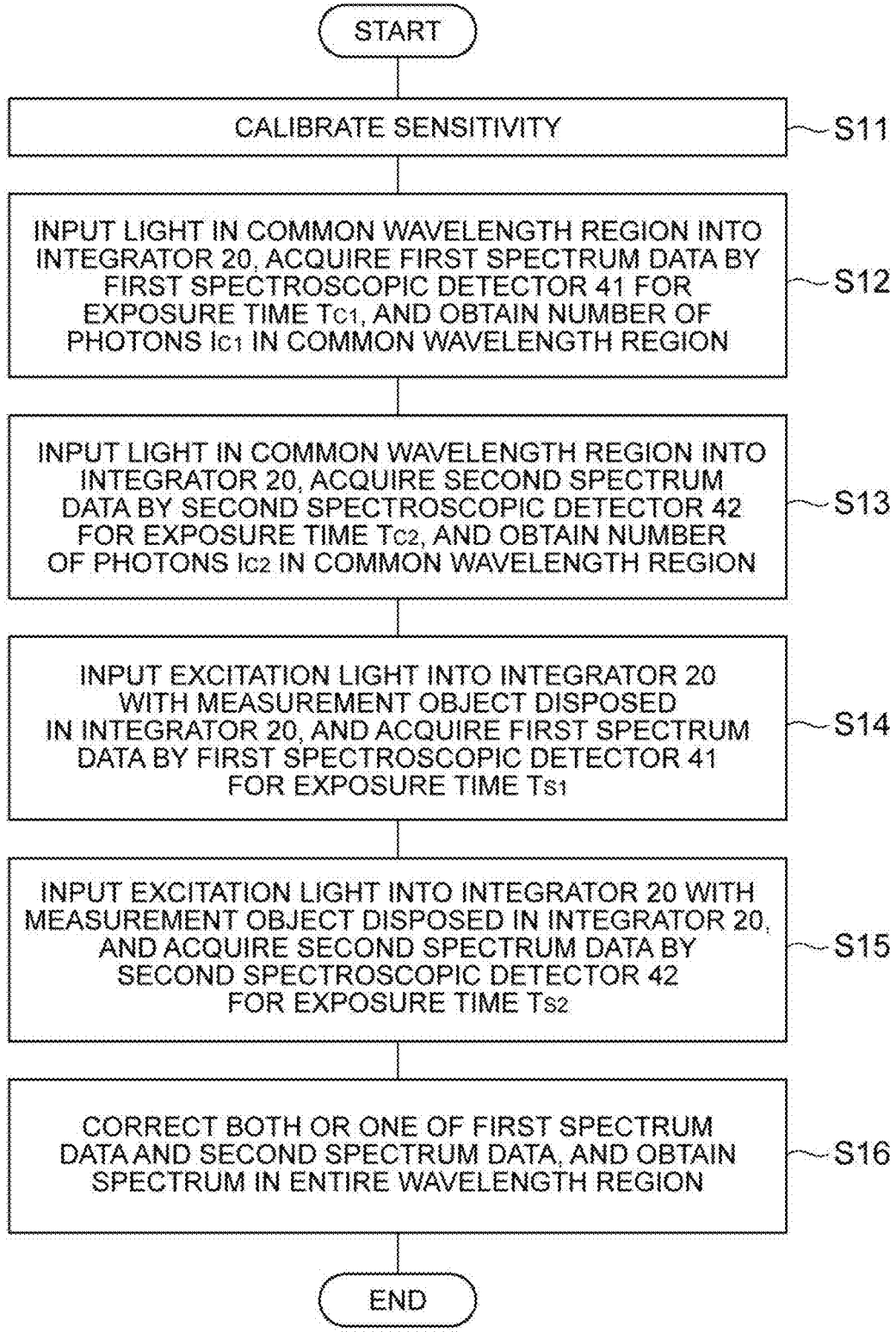
FIG. 4 is a flowchart for describing the procedure of obtaining a spectrum of an entire wavelength region.

In the first operation example of the present embodiment, the spectrum of the entire wavelength region including both the first wavelength region and the second wavelength region is obtained and displayed through the procedure in accordance with the flow in FIG. 4.

In step S11, the standard light in the first wavelength region Whose spectrum is known is input to the integrator 20 and the light output from the integrator 20 at that time is dispersed by the first spectroscopic detector 41 and the spectrum is acquired, and thus, the sensitivity of the first spectroscopic detector 41 is calibrated. In a similar manner, the standard light in the second wavelength region whose spectrum is known is input to the integrator 20 and the light output from the integrator 20 at that time is dispersed by the second spectroscopic detector 42 and the spectrum is acquired, and thus, the sensitivity of the second spectroscopic detector 42 is calibrated. In the subsequent steps, the spectrum after sensitivity calibration is obtained.

In step S12, the reference light in the common wavelength region is input to the internal space 21 of the integrator 20, the light in the common wavelength region is received by the first spectroscopic detector 41, the first spectrum data for an exposure time $T_{C1}$ is acquired, and based on the first spectrum data, the analysis unit 50 obtains the number of photons $I_{C1}$ in the common wavelength region. In step S13, the same reference light in the common wavelength region is input to the internal space 21 of the integrator 20, the light in the common wavelength region is received by the second spectroscopic detector 42, the second spectrum data for an exposure time $T_{C2}$ is acquired, and based on the second spectrum data, the analysis unit 50 obtains the number of photons $I_{C2}$ in the common wavelength region. Then, the analysis unit 50 stores the ratio between the number of photons $I_{C1}$ in the common wavelength region of the first spectrum data and the number of photons $I_{C2}$ in the common wavelength region of the second spectrum data as the correction value. Here, storing the number of photons $I_{C1}$ and the number of photons $I_{C2}$ in the analysis unit 50 and calculating the ratio whenever necessary are the same as storing the correction value in the analysis unit 50.

Figure 5:
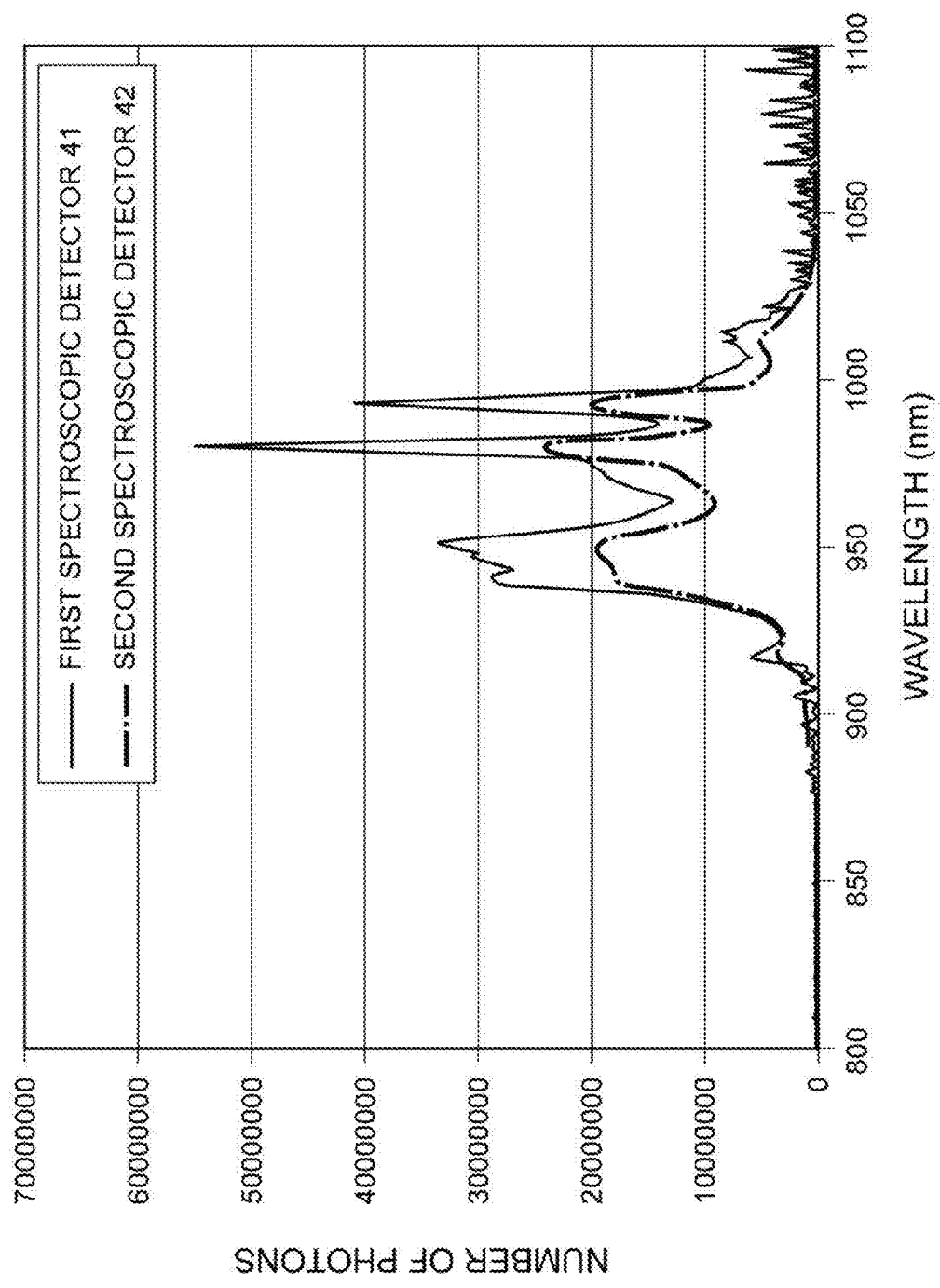
FIG. 5 is a diagram illustrating an example of the first spectrum and the second spectrum obtained in steps S12 and S13.

FIG. 5 is a diagram illustrating an example of the first spectrum and the second spectrum obtained in steps S12 and S13. The numbers of photons $I_{C1}$ and $I_{C2}$ can be obtained as the integrated values of the spectrum data in the common wavelength region. The number of photons to be obtained later can also be obtained similarly as the integrated value of the spectrum data in a predetermined wavelength region.

In step S14, the excitation light is input to the integrator 20 in a state where the measurement object is disposed in the internal space 21 of the integrator 20, the light in the first wavelength region is received by the first spectroscopic detector 41, and the first spectrum data for an exposure time $T_{S1}$ is acquired. In step S15, the excitation light is similarly input to the integrator 20 in a state where the measurement object is disposed in the internal space 21 of the integrator 20, the light in the second wavelength region is received by the second spectroscopic detector 42, and the second spectrum data for an exposure time $T_{S2}$ is acquired.

In step S16, both or one of the first spectrum data obtained in step S14 and the second spectrum data obtained in step S15 is corrected by the analysis unit 50 on the basis of the number of photons $I_{C1}$ obtained in step S12, the number of photons $I_{C2}$ obtained in step S13, the exposure time $T_{C1}$ in step S12, the exposure time $T_{C2}$ in step S13, the exposure time $T_{S1}$ in step S14, and the exposure time $T_{S2}$ in step S15. Thus, the spectrum in the entire wavelength region including both the first wavelength region and the second wavelength region is obtained. The spectrum in the entire wavelength region is displayed on the display unit 51.

When the correction is made on the energy basis in step S16, the data obtained by multiplying the second spectrum data on the energy basis by the correction coefficient (E) represented by Formula (1) below is connected to the first spectrum data on the energy basis, and thus, the spectrum of the entire wavelength region on the energy basis is obtained. Here, $I_{C1}/I_{C2}$ in Formula (1) is the correction value stored in the analysis unit 50.

[Formula 1]

$$\text{correction coefficient}(E) = \frac{I_{C1}}{I_{C2}} \times \frac{T_{S1}}{T_{C1}} \times \frac{T_{C2}}{T_{S2}} \quad (1)$$

When the correction is made on the number of photons basis in step S16, the data obtained by multiplying the second spectrum data on the number of photons basis by the correction coefficient (PN) represented by Formula (2) below is connected to the first spectrum data on the number of photons basis, and thus, the spectrum of the entire wavelength region on the number of photons basis is obtained. $\Delta\lambda_1$ is the wavelength resolution of the first spectroscopic detector 41 and $\Delta\lambda_2$ is the wavelength resolution of the second spectroscopic detector 42. $I_{C1}/I_{C2}$ in Formula (2) is the correction value stored in the analysis unit 50.

[Formula 2]

$$\text{correction coefficient}(PN) = \frac{I_{C1}}{I_{C2}} \times \frac{T_{S1}}{T_{C1}} \times \frac{T_{C2}}{T_{S2}} \times \frac{\Delta\lambda_1}{\Delta\lambda_2} \quad (2)$$

Here, in step S16 the data obtained by multiplying the first spectrum data by the reciprocal of the correction coefficient may be connected to the second spectrum data, and thus, the spectrum of the entire wavelength region is obtained. Further, the data obtained by multiplying the first spectrum data by an arbitrary coefficient $k_1$ may be connected to the data obtained by multiplying the second spectrum data by a coefficient $k_2$ (=the correction coefficient $\times k_1$), and thus, the spectrum of the entire wavelength region is obtained.

Here, the order of performing steps S12 to S15 may be determined arbitrarily. The exposure periods in steps S12 and S13 may partially overlap with each other. The exposure periods in steps S14 and S15 may partially overlap with each other.

Steps S11 to S13 may be performed before the spectroscopic measurement apparatus 1 is shipped from the factory, while steps S14 to S16 may be performed by the user of the spectroscopic measurement apparatus 1 after the shipment. The results obtained in steps S11 to S13 may be used in every measurement performed thereafter. Steps S11 to S13 may be performed every time prior to steps S14 to S16.

When the wavelength of the excitation light or the fluorescence is included in the common wavelength region, the excitation light or the fluorescence may be measured in steps S12 and S13.

Figure 6:
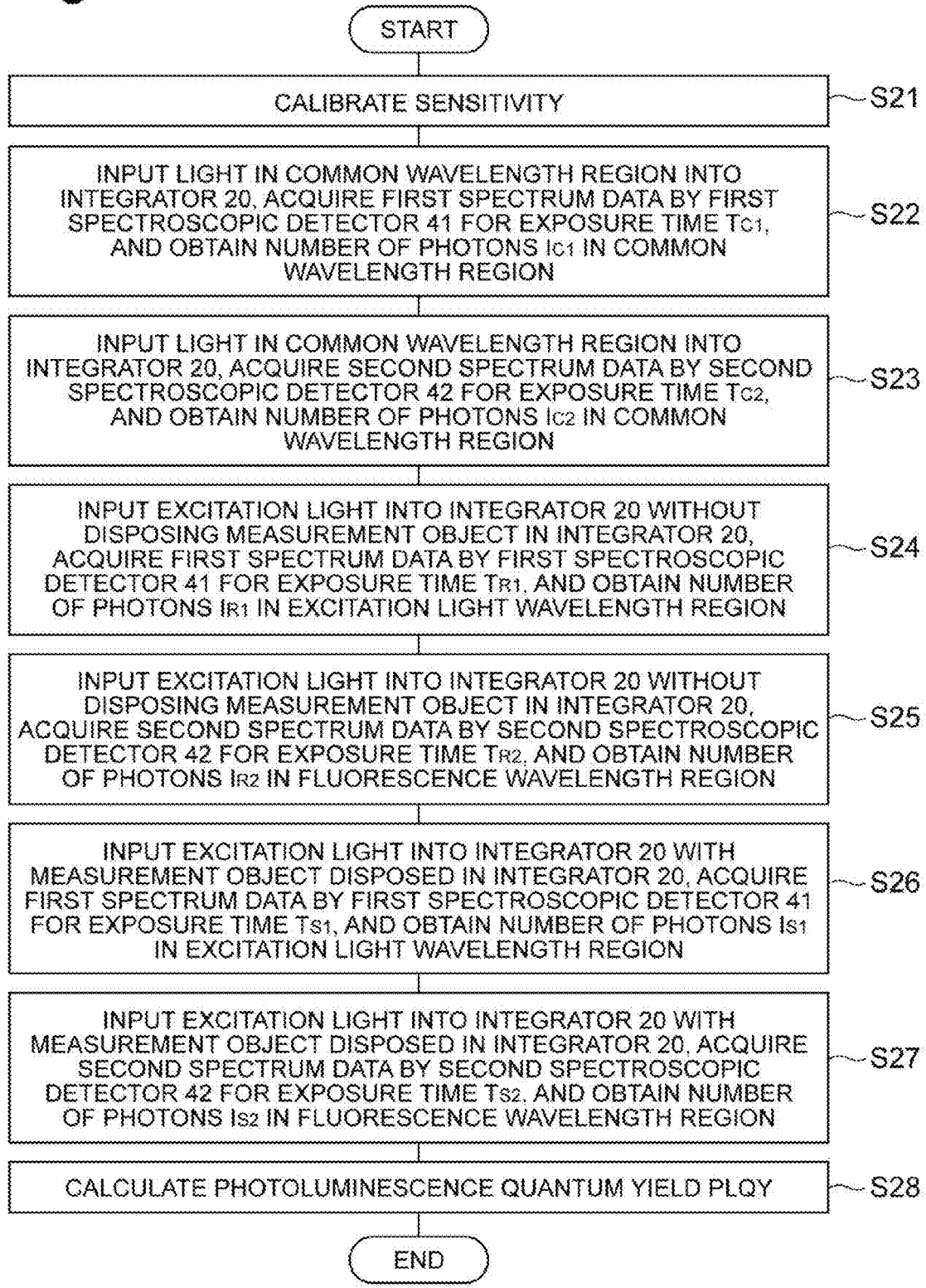
FIG. 6 is a flowchart for describing the procedure of evaluating a photoluminescence quantum yield of a measurement object.

In a second operation example of the present embodiment, the photoluminescence quantum yield of the measurement object is evaluated through the procedure in accordance with the flow in FIG. 6. Steps S21 to S23 in the second operation example are similar to steps S11 to S13 in the first operation example described above.

In steps S24 and S25, the reference measurement is performed in a state where the measurement object is not disposed in the internal space 21 of the integrator 20. In steps S26 and S27, the sample measurement is performed in a state where the measurement object is disposed in the internal space 21 of the integrator 20. When the measurement object is disposed in the internal space 21 with the object contained in the container in the sample measurement, the container is disposed in the internal space 21 in the reference measurement.

In step S24, the excitation light is input to the integrator 20 in a state where the measurement object is not disposed in the internal space 21 of the integrator 20, the light in the first wavelength region is received by the first spectroscopic detector 41, and thus, the first spectrum data for an exposure time $T_{R1}$ is acquired. Then, based on the first spectrum data, the analysis unit 50 obtains the number of photons $I_{R1}$ in the excitation light wavelength region.

In step S25, the excitation light is input to the integrator 20 in a state where the measurement object is not disposed in the internal space 21 of the integrator 20, the light in the second wavelength region is received by the second spectroscopic detector 42, and thus, the second spectrum data for an exposure time $T_{R2}$ is acquired. Then, based on the second spectrum data, the analysis unit 50 obtains the number of photons $I_{R2}$ in the fluorescence wavelength region.

In step S26, the excitation light is input to the integrator 20 in a state where the measurement object is disposed in the internal space 21 of the integrator 20, the light in the first wavelength region is received by the first spectroscopic detector 41, and thus, the first spectrum data for an exposure time $T_{S1}$ is acquired. Then, based on the first spectrum data, the analysis unit 50 obtains the number of photons $I_{S1}$ in the excitation light wavelength region.

In step S27, the excitation light is input to the integrator 20 in a state where the measurement object is disposed in the internal space 21 of the integrator 20, the light in the second wavelength region is received by the second spectroscopic detector 42, and thus, the second spectrum data for an exposure time $T_{S2}$ is acquired. Then, based on the second spectrum data, the analysis unit 50 obtains the number of photons $I_{S2}$ in the fluorescence wavelength region.

Here, the excitation light wavelength region and the fluorescence wavelength region in steps S24, S25, S26, and S27 may be set by the user of the spectroscopic measurement apparatus 1 through the input unit 52, or may be automatically set by the analysis unit 50 on the basis of the first spectrum data and the second spectrum data. The excitation light wavelength region in step S24 and the excitation light wavelength region in step S26 are the same wavelength region. The fluorescence wavelength region in step S25 and the fluorescence wavelength region in step S27 are the same wavelength region.

In step S28, the analysis unit 50 obtains the photoluminescence quantum yield PLQY of the measurement object from Formula (3) below on the basis of the exposure times $T_{C1}$, $T_{C2}$, $T_{R1}$, $T_{R2}$, $T_{S1}$, and $T_{S2}$ in the respective steps and the number of photons $I_{C1}$, $I_{C2}$, $I_{R1}$, $I_{R2}$, $I_{S1}$, and $I_{S2}$ obtained in the respective steps. Out of the four factors on the right side of this formula, the first factor is the photoluminescence quantum yield before the correction, the second factor is the correction factor related to the number of photons in the common wavelength region detected in steps S22 and S23, and the third factor and the fourth factor are the correction factors related to the exposure time in each step. The external quantum efficiency can be obtained by multiplying the absorptance of the measurement object and the internal quantum yield. Here, $I_{C1}/I_{C2}$ in Formula (3) is the correction value stored in the analysis unit 50.

[Formula 3]

$$PLQY = \frac{I_{S2} - I_{R2}}{I_{R1} - I_{S1}} \times \frac{I_{C1}}{I_{C2}} \times \frac{T_{S1}}{T_{C1}} \times \frac{T_{C2}}{T_{S2}} \qquad (3)$$

Here, the order of steps S22 to S27 is arbitrary. The exposure periods in steps S22 and S23 may partially overlap with each other. The exposure periods in steps S24 and S25 may partially overlap with each other. The exposure periods in steps S26 and S27 may partially overlap with each other.

Steps S21 to S23 may be performed before the spectroscopic measurement apparatus 1 is shipped from the factory, while steps S24 to S28 may be performed by the user of the spectroscopic measurement apparatus 1 after the shipment. The results obtained in steps S21 to S23 may be used in every measurement performed thereafter. Steps S21 to S23 may be performed every time prior to steps S24 to S28.

Figure 7:
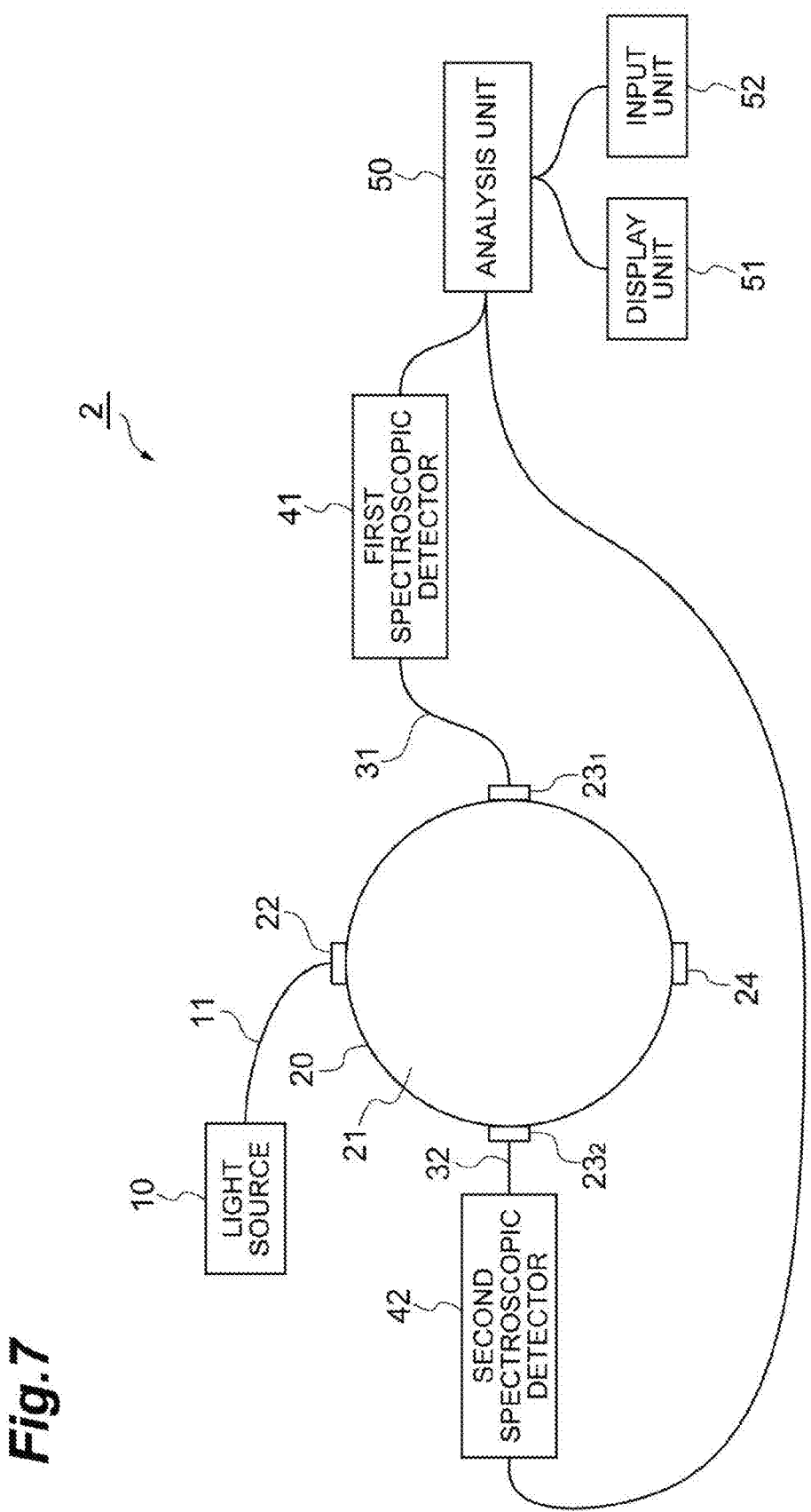
FIG. 7 is a diagram illustrating a configuration of a spectroscopic measurement apparatus 2.

FIG. 7 is a diagram illustrating a configuration of a spectroscopic measurement apparatus 2. The spectroscopic measurement apparatus 2 illustrated in FIG. 7 is different from the spectroscopic measurement apparatus 1 illustrated in FIG. 1 in that the integrator 20 includes a first spectroscopic output portion $23_1$ and a second spectroscopic output portion $23_2$ instead of the light output portion 23. The first output light guide 31 guides the light output from the first spectroscopic output portion $23_1$ of the integrator 20 to the first spectroscopic detector 41. The second output light guide 32 guides the light output from the second spectroscopic output portion $23_2$ of the integrator 20 to the second spectroscopic detector 42.

With such a configuration, by providing a first spectroscopic filter on the optical path between the first spectroscopic output portion $23_1$ and the first spectroscopic detector 41, the power of the light in the first wavelength region to be input to the first spectroscopic detector 41 can be adjusted easily and the exposure time of the first spectroscopic detector 41 can be easily adjusted. Further, by providing a second spectroscopic filter on the optical path between the second spectroscopic output portion $23_2$ and the second spectroscopic detector 42, the power of the light in the second wavelength region to be input to the second spectroscopic detector 42 can be adjusted easily and the exposure time of the second spectroscopic detector 42 can be easily adjusted.

Figure 8:
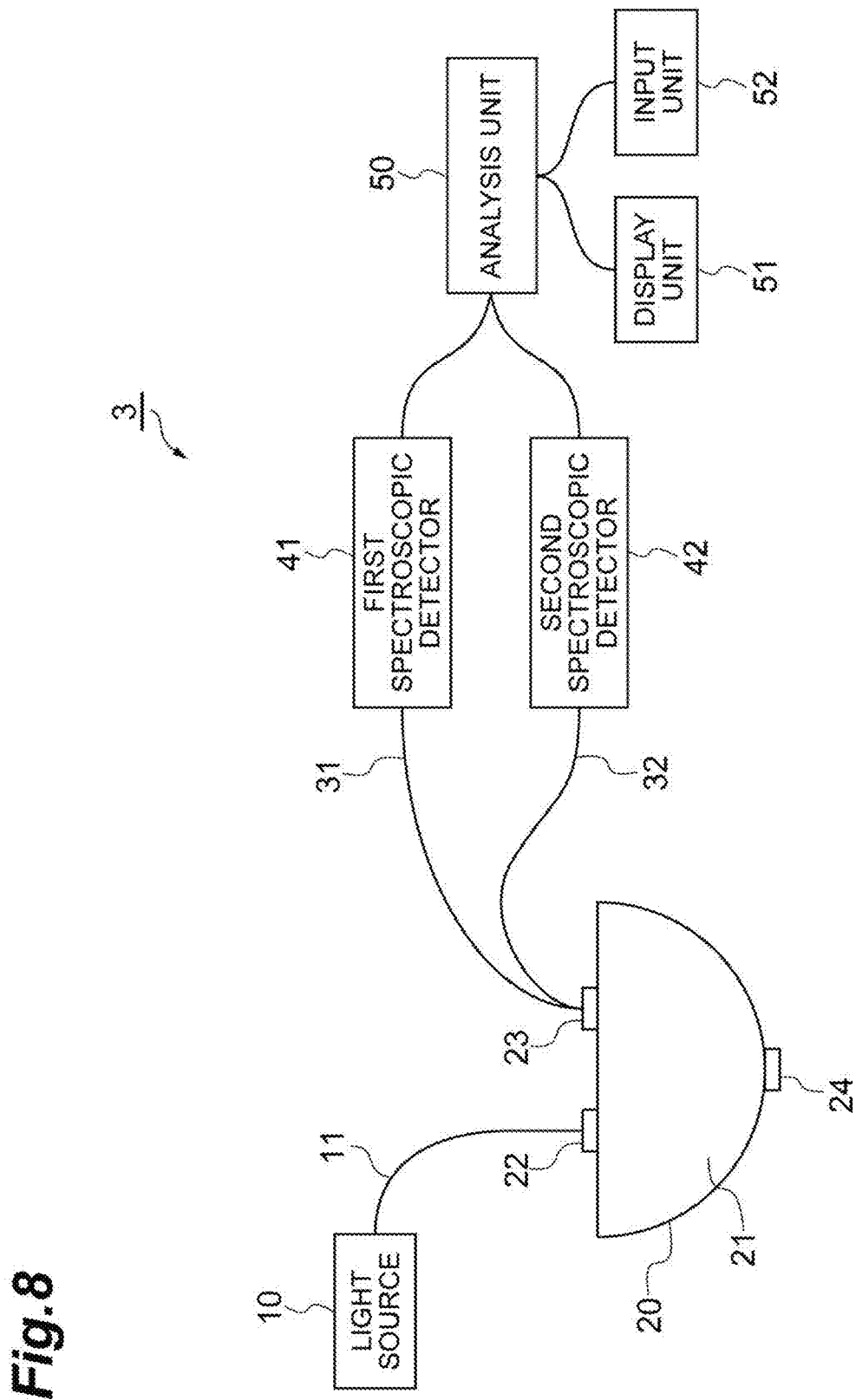
FIG. 8 is a diagram illustrating a configuration of a spectroscopic measurement apparatus 3.

FIG. 8 is a diagram illustrating a configuration of a spectroscopic measurement apparatus 3. While the integrator 20 of the spectroscopic measurement apparatuses 1 and 2 illustrated in FIG. 1 and FIG. 7 is the integrating sphere, the integrator 20 of the spectroscopic measurement apparatus 3 illustrated in FIG. 8 is the integrating hemisphere. The internal space 21 of the integrator 20 is the hemisphere whose inner wall of a hemispherical portion has a wall surface with high reflectance and excellent diffuseness, and whose planar portion is a flat mirror with high reflectance. The light input portion 22 and the light output portion 23 may be provided in any place in the hemispherical portion and the planar portion.

Even when the spectroscopic measurement apparatus 2 or 3 is used, the spectroscopic measurement can be performed for the measurement target light in the wider wavelength region as in the case of using the spectroscopic measurement apparatus 1.

In addition to the first spectroscopic detector and the second spectroscopic detector, a third spectroscopic detector for acquiring spectrum data in a third wavelength region may be provided. In this case, for example, a part of the second wavelength region on the short-wavelength side overlaps with a part of the first wavelength region on the long-wavelength side, and a part of the second wavelength region on the long-wavelength side overlaps with a part of the third wavelength region on the short-wavelength side. Thus, the spectroscopic measurement of the measurement target light in the wider wavelength region can be performed.

In general, the intensity of the excitation light is several digits higher than that of the emission light. In view of this, a filter that selectively attenuates the light in the excitation light wavelength region out of the excitation light wavelength region and the emission light wavelength region is preferably provided on the optical path between the integrator and the spectroscopic detector that detects the light in the excitation light wavelength region. This enables the spectroscopic measurement in the appropriate exposure time without saturating each spectroscopic detector.

In the above embodiment, the emission light (for example, fluorescence) wavelength is longer than the excitation light wavelength. However, on the contrary, the emission light wavelength may be shorter than the excitation light wavelength. In the latter case, the emission light is, for example, the up-conversion light. In the case of measuring the spectrum including both the excitation light and the up-conversion light or measuring the luminous efficiency of the up-conversion light using the spectroscopic measurement apparatus 1, the first wavelength region on the short-wavelength side detected by the first spectroscopic detector 41 includes the up-conversion light wavelength and the second wavelength region on the long-wavelength side detected by the second spectroscopic detector 42 includes the excitation light wavelength.

In order to generate the up-conversion light, it is necessary to increase the intensity density of the excitation light with which the measurement object is irradiated. Here, the luminous efficiency of the up-conversion light is low, and therefore, in the case of performing the evaluation of the photoluminescence quantum yield (internal quantum efficiency) in which both the intensity of the absorbed excitation light and the intensity of the up-conversion light need to be acquired, the spectroscopic detector is possibly saturated because of the excitation light with the high intensity. Further, some of the up-conversion luminescence materials have higher photoluminescence quantum yield when irradiated with the excitation light having the higher intensity density. In those materials, the spectroscopic detector is possibly saturated due to the up-conversion light having the high intensity.

In view of the above, when the luminous efficiency of the up-conversion light is measured, it is preferable that, not only the excitation light output from the integrator 20 is appropriately attenuated, but also the up-conversion light output from the integrator 20 is appropriately attenuated. A filter unit for performing such attenuation has the transmission spectrum that the attenuation rate for the excitation light is larger than that for the up-conversion light.

Hereinafter, a spectroscopic measurement apparatus preferably used to measure the luminous efficiency of the up-conversion light is described with reference to FIG. 9 to FIG. 12.

Figure 9:
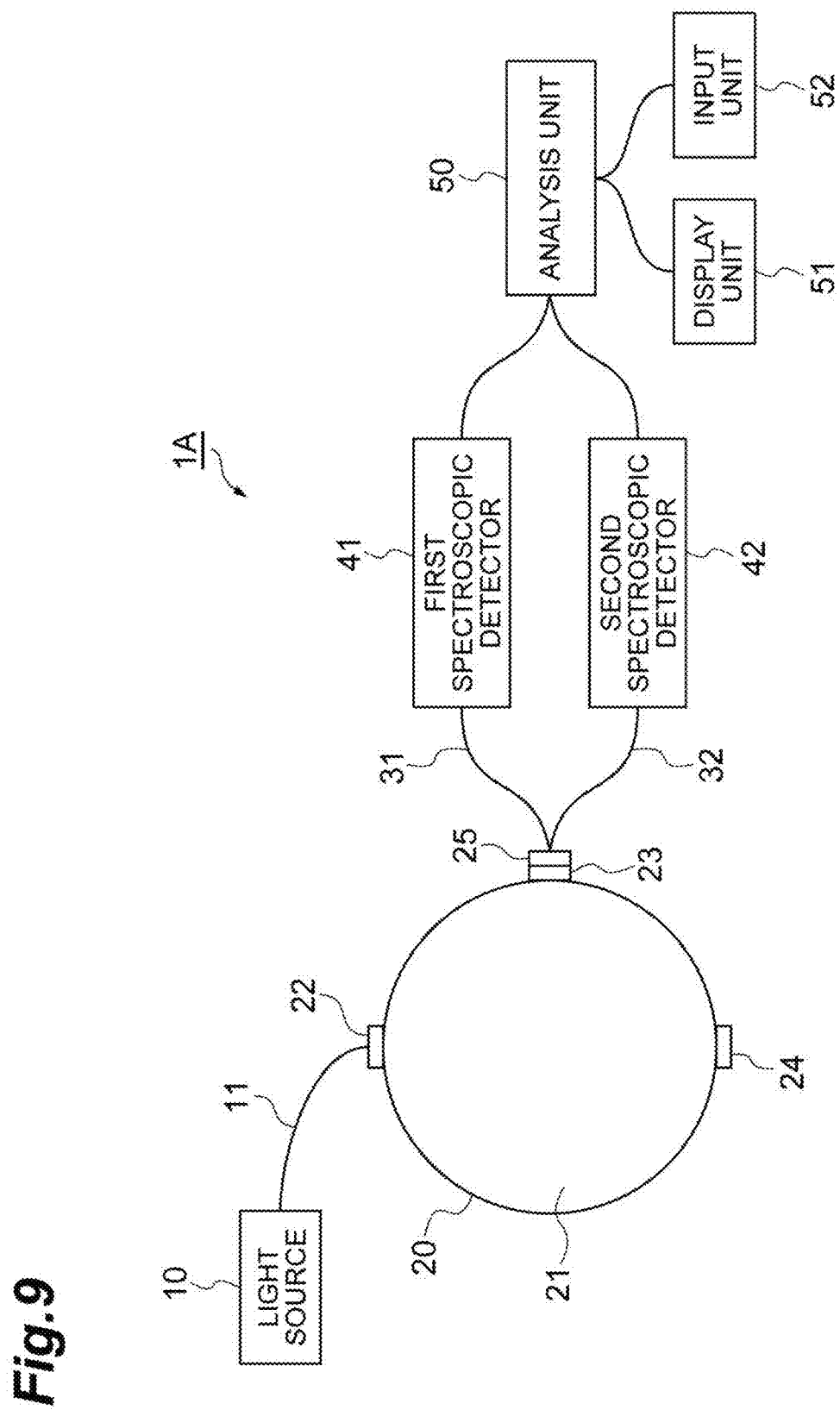
FIG. 9 is a diagram illustrating a configuration of a spectroscopic measurement apparatus 1A.

FIG. 9 is a diagram illustrating a configuration of a spectroscopic measurement apparatus 1A. The spectroscopic measurement apparatus 1A illustrated in FIG. 9 is different from the spectroscopic measurement apparatus 1 illustrated in FIG. 1 in that the integrator 20 has a filter attachment portion 25 for attaching a filter unit. The filter attachment portion 25 is provided for the light output portion 23 of the integrator 20, and disposes the above-described filter unit that attenuates the light output from the light output portion 23.

Figure 10:
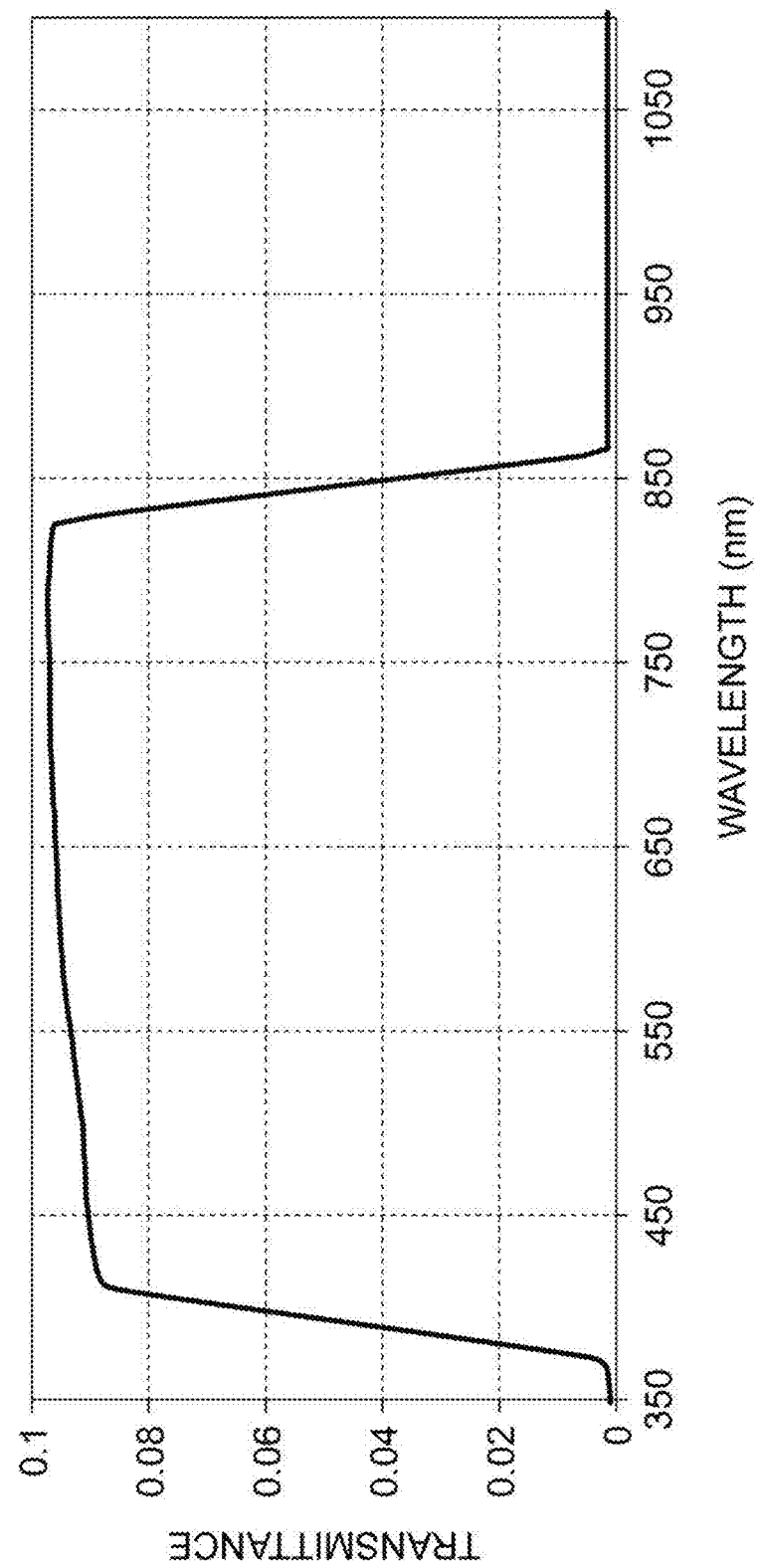
FIG. 10 is a diagram illustrating an example of a transmission spectrum of a filter unit attached to a filter attachment portion 25 of an integrator 20.

FIG. 10 is a diagram illustrating an example of the transmission spectrum of the filter unit attached to the filter attachment portion 25 of the integrator 20. In the transmission characteristic of the filter unit, the attenuation rate in the excitation light wavelength region (wavelength region including 980 nm) is larger than the attenuation rate in the up-conversion light wavelength region. The filter unit attenuates the light output from the light output portion 23 in accordance with such a transmission spectrum. This filter unit may include a first filter that selectively attenuates the excitation light on the long-wavelength side out of the excitation light and the up-conversion light, and a second filter that attenuates both the excitation light and the up-conversion light.

The first filter may be a short-pass filter or a band-pass filter. The second filter may be an ND filter or may be formed of a light-reflective material. In the latter case, the light-reflective material may be Spectralon (registered trademark), which is the material with high reflectance and excellent diffuseness to be provided for the inner wall surface of the integrator 20. Spectralon has approximately constant reflectance over a wide wavelength region from the visible range to the near-infrared range. A Spectralon filter formed by a sheet of Spectralon can be used as the second filter. Such a Spectralon filter can be used not only as the second filter but also as a part of the inner wall surface of the integrator 20 that diffuses and reflects the light.

Figure 11:
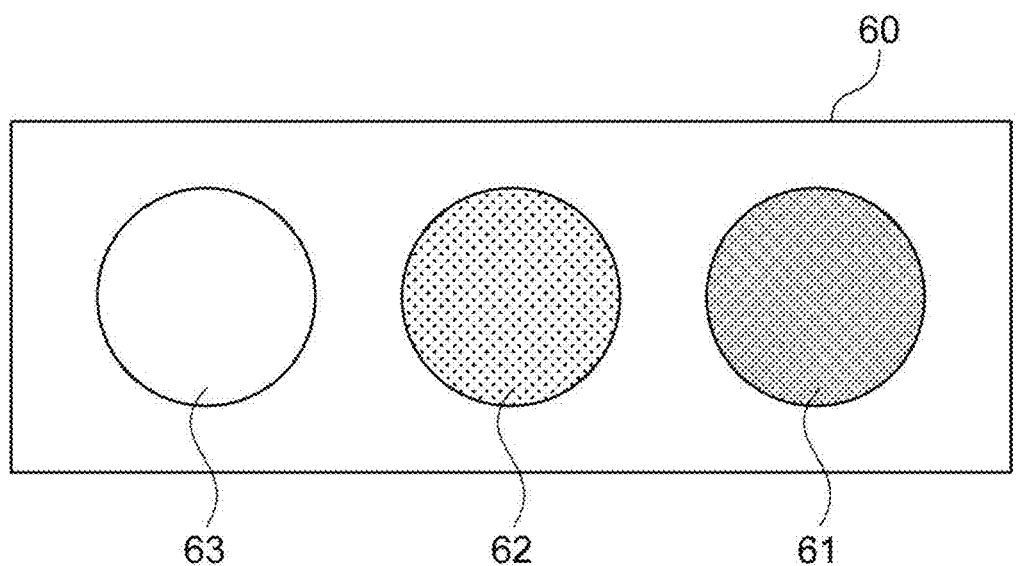
FIG. 11 is a diagram illustrating an example of a filter set 60 attached to a filter attachment portion 25 of a integrator 20.

In the filter attachment portion 25 of the integrator 20, the filter is preferably replaceable freely on the optical path with the filter unit having the transmission spectrum as illustrated in FIG. 10, or a filter having another transmission spectrum. FIG. 11 is a diagram illustrating an example of a filter set 60 attached to the filter attachment portion 25 of the integrator 20. This filter set 60 is formed by arranging side by side a filter unit 61 having the transmission spectrum as illustrated in FIG. 10, a short-pass filter 62 that selectively attenuates the excitation light out of the excitation light and the up-conversion light, and an opening (without filter) 63. Any filter can be disposed on the optical path by sliding the filter set 60 in the filter attachment portion 25.

Figure 12:
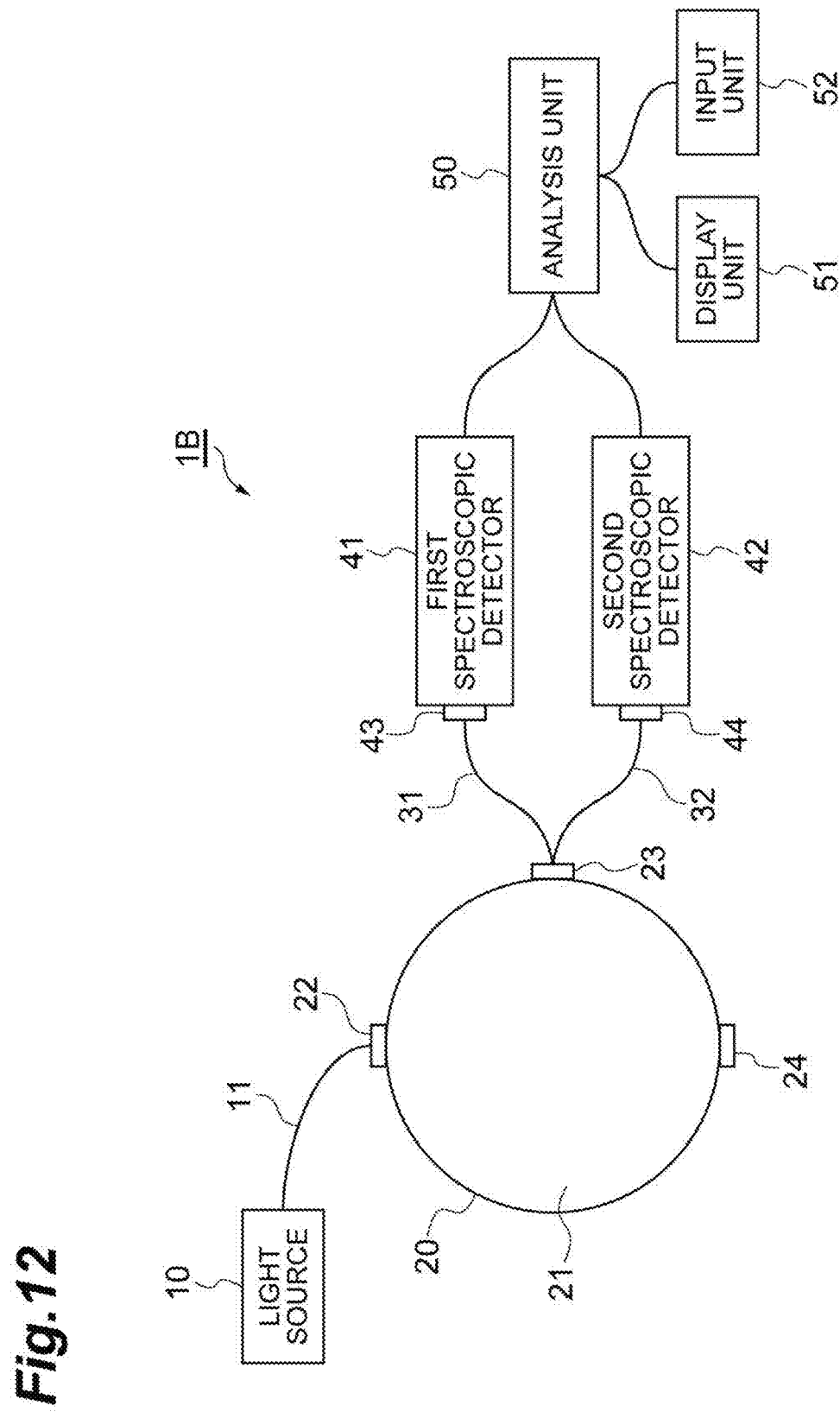
FIG. 12 is a diagram illustrating a configuration of a spectroscopic measurement apparatus 1B.

FIG. 12 is a diagram illustrating a configuration of a spectroscopic measurement apparatus 1B. The spectroscopic measurement apparatus 1B illustrated in FIG. 12 is different from the spectroscopic measurement apparatus 1 illustrated in FIG. 1 in that a filter attachment portion 43 is provided on the light input portion of the first spectroscopic detector 41 and a filter attachment portion 44 is provided on the light input portion of the second spectroscopic detector 42. These filter attachment portions 43 and 44 are used to dispose the above-described filter unit 61 or the filter set 60 for attenuating the light to be input to the spectroscopic detectors 41 and 42.

In the spectroscopic measurement apparatus 1B, the filter unit disposed on the light input portion of each of the filter attachment portions 43 and 44 may have either the same transmission spectrum or the different transmission spectrum. In the latter case, it is only necessary that the filter provided at the light input portion of the first spectroscopic detector 41 that performs spectroscopic measurement of the up-conversion light wavelength region selectively attenuates the up-conversion light wavelength region, and that the filter provided at the light input portion of the second spectroscopic detector 42 that performs spectroscopic measurement of the excitation light wavelength region selectively attenuates the excitation light wavelength region.

In addition to providing the above-described filter unit or instead of providing the filter unit, the exposure time of each of the spectroscopic detectors 41 and 42 may be set appropriately. As described above, the second spectroscopic detector 42 including the InGaAs linear image sensor as the optical sensor is less sensitive than the first spectroscopic detector 41 including the silicon linear image sensor as the optical sensor, and thus, it is preferable that the transmission spectrum of the filter and the exposure time are set appropriately in consideration of the sensitivity of each of the spectroscopic detectors 41 and 42.

When the above filter unit 61 that attenuates the excitation light or the emission light is provided, the analysis unit 50 corrects the spectroscopic spectrum data acquired by the spectroscopic detectors 41 and 42 on the basis of the transmission spectrum data of the filter unit 61, and performs the above-described analysis based on the spectroscopic spectrum data before the attenuation.

The transmission spectrum of the filter unit is obtained as below. In this state, the measurement object is not disposed in the internal space 21 of the integrator 20. In a case where the filter unit 61 or the opening (without filter) 63 is disposed on the optical path in the filter attachment portion 25, the standard light is input to the integrator 20 and the light output from the integrator 20 at that time is dispersed by the spectroscopic detectors 41 and 42, and thus, the spectrum is acquired.

The spectrum data acquired by the first spectroscopic detector 41 when the filter unit 61 is disposed on the optical path is $S_{11}(\lambda)$, and the spectrum data acquired by the first spectroscopic detector 41 when the opening 63 is disposed on the optical path is $S_{10}(\lambda)$. The exposure time when the spectrum data $S_{11}(\lambda)$ and $S_{10}(\lambda)$ are acquired is set to be the same. The spectrum data acquired by the second spectroscopic detector 42 when the filter unit 61 is disposed on the optical path is $S_{21}(\lambda)$, and the spectrum data acquired by the second spectroscopic detector 42 when the opening 63 is disposed on the optical path is $S_{20}(\lambda)$. The exposure time when the spectrum data $S_{21}(\lambda)$ and $S_{20}(\lambda)$ are acquired is set to be the same.

The transmission spectrum data $T_1(\lambda)$ of the filter unit 61 for the light input to the first spectroscopic detector 41 is obtained by the following Formula (4a). The transmission spectrum data $T_2(\lambda)$ of the filter unit 61 for the light input to the second spectroscopic detector 42 is obtained by the following Formula (4b). $\lambda$ is the wavelength. The transmission spectrum data $T_1(\lambda)$ and $T_2(\lambda)$ are stored in the storage unit of the analysis unit 50.

[Formula 4]

$$T_1(\lambda) = S_{11}(\lambda)/S_{10}(\lambda) \tag{4a}$$

$$T_2(\lambda) = S_{21}(\lambda)/S_{20}(\lambda) \tag{4b}$$

In each of the reference measurement and the sample measurement, the respective spectroscopic spectrum data before the attenuation by the filter unit 61 can be obtained by dividing the spectroscopic spectrum data, acquired by the first spectroscopic detector 41, in a state where the filter unit 61 is disposed on the optical path, by the transmission spectrum data $T_1(\lambda)$, and dividing the spectroscopic spectrum data, acquired by the second spectroscopic detector 42, by the transmission spectrum data $T_2(\lambda)$. Using the thus corrected spectroscopic spectrum data, the spectrum in the entire wavelength region is calculated and the photoluminescence quantum yield of the measurement object is evaluated.

Here, when the first spectroscopic detector 41 performs spectroscopic detection of the emission light (the up-conversion light) and the second spectroscopic detector 42 performs spectroscopic detection of the excitation light, the procedure is the opposite to that of the above-described case, and in accordance with this, the PLQY calculation formula is different. The photoluminescence quantum yield PLQY of the up-conversion luminescence material is represented by the following Formula (5). Each parameter in the right side of this formula is similar to that of Formula (3). Here, $I_{C2}/I_{C1}$ in Formula (3) is the correction value stored in the analysis unit 50.

Embodiments of the present invention have been described, but the present invention is not limited to the above embodiments and various modifications are possible. Further, the present invention may be modified within the range not departing from the content described in claims and may be applied to others.

For example, the spectroscopic spectrum data is not limited to the data representing the number of photons for each wavelength, but may be the data representing the detection intensity for each wavelength. In this case, from the data representing the detection intensity for each wavelength, the intensity integrated value of the common wavelength region in the first spectrum data may be obtained, and further, the intensity integrated value of the common wavelength region in the second spectrum data may be obtained, and then, the correction value which is the ratio of these intensity integrated values may be obtained. Further, the numbers of photons $I_{C1}$, $I_{C2}$, $I_{R1}$, $I_{R2}$, $I_{S1}$, and $I_{S2}$ may be obtained from the data representing the detection intensity for each wavelength.

[Formula 5]

$$PLQY = \frac{I_{S1} - I_{R1}}{I_{R2} - I_{S2}} \times \frac{I_{C2}}{I_{C1}} \times \frac{T_{S2}}{T_{C2}} \times \frac{T_{C1}}{T_{S1}} \tag{5}$$

The spectroscopic measurement apparatus according to the embodiment includes (1) an integrator including an internal space in which a measurement object is disposed, a light input portion for inputting light from outside to the internal space, and a light output portion for outputting light from the internal space to the outside; (2) a first spectroscopic detector for dispersing light in a first wavelength region in the light output from the light output portion and acquiring first spectrum data for a first exposure time; (3) a second spectroscopic detector for dispersing light in a second wavelength region partially overlapping with the first wavelength region in the light output from the light output portion and acquiring second spectrum data for a second exposure time; and (4) an analysis unit for analyzing the first spectrum data and the second spectrum data on the basis of the first exposure time and the second exposure time.

The spectroscopic measurement method according to the embodiment is a method (1) using an integrator including an internal space in which a measurement object is disposed, a light input portion for inputting light from outside to the internal space, and a light output portion for outputting light from the internal space to the outside, and for performing spectroscopic measurement, and the method includes (2) inputting light from the light input portion of the integrator to the internal space; (3) dispersing light in a first wavelength region in the light output from the light output portion and acquiring first spectrum data for a first exposure time by a first spectroscopic detector; (4) dispersing light in a second wavelength region partially overlapping with the first wavelength region in the light output from the light output portion and acquiring second spectrum data for a second exposure time by a second spectroscopic detector; and (5) analyzing the first spectrum data and the second spectrum data on the basis of the first exposure time and the second exposure time by an analysis unit.

In the spectroscopic measurement apparatus and method of the above configuration, when light of a common wavelength region, which is a wavelength region in which the first wavelength region and the second wavelength region overlap, is input from the light input portion of the integrator to the internal space, the analysis unit may obtain the number of photons in the common wavelength region on the basis of the first spectrum data and obtain the number of photons in the common wavelength region on the basis of the second spectrum data, correct both or one of the first spectrum data and the second spectrum data on the basis of these numbers of photons, the first exposure time, and the second exposure time, and obtain a spectrum in an entire wavelength region including both the first wavelength region and the second wavelength region.

Further, in the spectroscopic measurement apparatus and method of the above configuration, the analysis unit may calculate and store a correction value on the basis of the first spectrum data in the common wavelength region and the second spectrum data in the common wavelength region which are acquired when the light in the common wavelength region, which is the wavelength region in which the first wavelength region and the second wavelength region overlap, is input from the light input portion of the integrator to the internal space.

Further, in the spectroscopic measurement apparatus, the analysis unit may store a correction value calculated based on the first spectrum data and the second spectrum data in a common wavelength region which is a wavelength region in which the first wavelength region and the second wavelength region overlap. Further, in the spectroscopic measurement method, by the analysis unit, a correction value calculated based on the first spectrum data and the second spectrum data in a common wavelength region which is a wavelength region in which the first wavelength region and the second wavelength region overlap may be stored.

The above correction value may be calculated based on the number of photons in the common wavelength region in the first spectrum data and the number of photons in the common wavelength region in the second spectrum data. Further, in the spectroscopic measurement apparatus, the analysis unit may obtain the number of photons in the common wavelength region on the basis of the first spectrum data, obtain the number of photons in the common wavelength region on the basis of the second spectrum data, and calculate the correction value on the basis of these numbers of photons. Further, in the spectroscopic measurement method, by the analysis unit, the number of photons in the common wavelength region may be obtained on the basis of the first spectrum data, the number of photons in the common wavelength region may be obtained on the basis of the second spectrum data, and the correction value may be calculated on the basis of these numbers of photons.

Further, the above correction value may be calculated based on the intensity integrated value in the common wavelength region in the first spectrum data and the intensity integrated value in the common wavelength region in the second spectrum data. Further, in the spectroscopic measurement apparatus, the analysis unit may obtain an intensity integrated value in the common wavelength region on the basis of the first spectrum data, obtain an intensity integrated value in the common wavelength region on the basis of the second spectrum data, and calculate the correction value on the basis of these intensity integrated values. Further, in the spectroscopic measurement method, by the analysis unit, an intensity integrated value in the common wavelength region may be obtained on the basis of the first spectrum data, an intensity integrated value in the common wavelength region may be obtained on the basis of the second spectrum data, and the correction value may be calculated on the basis of these intensity integrated values.

Further, in the spectroscopic measurement apparatus, the analysis unit may correct both or one of the first spectrum data and the second spectrum data on the basis of the correction value, the first exposure time, and the second exposure time and obtain a spectrum in an entire wavelength region including both the first wavelength region and the second wavelength region. Further, in the spectroscopic measurement method, by the analysis unit, both or one of the first spectrum data and the second spectrum data may be corrected on the basis of the correction value, the first exposure time, and the second exposure time and a spectrum in an entire wavelength region including both the first wavelength region and the second wavelength region may be obtained.

Further, in the spectroscopic measurement apparatus and method of the above configuration, when excitation light is input from the light input portion of the integrator to the internal space in a state where a measurement object which emits emission light by incidence of the excitation light is not disposed in the internal space, the analysis unit may obtain the number of photons in an excitation light wavelength region on the basis of the first spectrum data and obtain the number of photons in an emission light wavelength region on the basis of the second spectrum data, when the excitation light is input from the light input portion of the integrator to the internal space in a state where the measurement object is disposed in the internal space, the analysis unit may obtain the number of photons in the excitation light wavelength region on the basis of the first spectrum data and obtain the number of photons in the emission light wavelength region on the basis of the second spectrum data, and based on these numbers of photons, the correction value, and the first exposure time and the second exposure time, the analysis unit may evaluate the luminous efficiency of the measurement object.

Further, in the spectroscopic measurement apparatus and method of the above configuration, the second wavelength region may be on a long-wavelength side compared to the first wavelength region, and the second exposure time may be longer than the first exposure time.

Further, in Formula (1), Formula (2), Formula (3), or Formula (5) described above, for the first spectroscopic detector 41, the exposure time $T_{R1}$ in a case where the measurement object is not disposed may be used, instead of the exposure time $T_{S1}$ in a case where the measurement object is disposed. In this case, for the second spectroscopic detector 42, the exposure time $T_{R2}$ in a case where the measurement object is not disposed is used instead of the exposure time $T_{S2}$ in a case where the measurement object is disposed.

INDUSTRIAL APPLICABILITY

The present invention is applicable as a spectroscopic measurement apparatus and a spectroscopic measurement method that can perform spectroscopic measurement of measurement target light in a wider wavelength region.

REFERENCE SIGNS LIST 1, 1A, 1B, 2, 3—spectroscopic measurement apparatus, 10—light source, 11—input light guide, 20—integrator, 21—internal space, 22—light input portion, 23—light output portion, 24—sample attachment portion, 25—filter attachment portion, 31—first output light guide, 32—second output light guide, 41—first spectroscopic detector, 42—second spectroscopic detector, 43, 44—filter attachment portion, 50—analysis unit, 51—display unit, 52—input unit, 60—filter set, 61—filter unit.

The invention claimed is:

1. A spectroscopic measurement apparatus comprising:
an integrator including an internal space in which a measurement object is disposed, a light input portion configured to input light from outside to the internal space, and a light output portion configured to output light from the internal space to the outside;
a first spectroscopic detector configured to disperse light of a first wavelength region in the light output from the light output portion and acquire first spectrum data for a first exposure time;
a second spectroscopic detector configured to disperse light of a second wavelength region partially overlapping with the first wavelength region in the light output from the light output portion and acquire second spectrum data for a second exposure time; and
an analysis unit configured to analyze the first spectrum data and the second spectrum data on the basis of the first exposure time and the second exposure time.

2. The spectroscopic measurement apparatus according to claim 1, wherein the analysis unit is configured to store a correction value calculated based on the first spectrum data and the second spectrum data in a common wavelength region which is a wavelength region in which the first wavelength region and the second wavelength region overlap.

3. The spectroscopic measurement apparatus according to claim 2, wherein the analysis unit is configured to obtain the number of photons in the common wavelength region on the basis of the first spectrum data, obtain the number of photons in the common wavelength region on the basis of the second spectrum data, and calculate the correction value on the basis of these numbers of photons.

4. The spectroscopic measurement apparatus according to claim 2, wherein the analysis unit is configured to obtain an intensity integrated value in the common wavelength region on the basis of the first spectrum data, obtain an intensity integrated value in the common wavelength region on the basis of the second spectrum data, and calculate the correction value on the basis of these intensity integrated values.

5. The spectroscopic measurement apparatus according to claim 2, wherein the analysis unit is configured to correct at least one of the first spectrum data and the second spectrum data on the basis of the correction value, the first exposure time, and the second exposure time and obtain a spectrum in an entire wavelength region including both the first wavelength region and the second wavelength region.

6. The spectroscopic measurement apparatus according to claim 2, wherein
when excitation light is input from the light input portion of the integrator to the internal space in a state where a measurement object which emits emission light by incidence of the excitation light is not disposed in the internal space, the analysis unit obtains the number of photons in an excitation light wavelength region on the basis of the first spectrum data and obtains the number of photons in an emission light wavelength region on the basis of the second spectrum data;
when the excitation light is input from the light input portion of the integrator to the internal space in a state where the measurement object is disposed in the internal space, the analysis unit obtains the number of photons in the excitation light wavelength region on the basis of the first spectrum data and obtains the number of photons in the emission light wavelength region on the basis of the second spectrum data; and
based on these numbers of photons, the correction value, and the first exposure time and the second exposure time, the analysis unit evaluates luminous efficiency of the measurement object.

7. The spectroscopic measurement apparatus according to claim 1, wherein the second wavelength region is on a long-wavelength side compared to the first wavelength region, and the second exposure time is longer than the first exposure time.

8. A spectroscopic measurement method for performing spectroscopic measurement using an integrator including an internal space in which a measurement object is disposed, a light input portion configured to input light from outside to the internal space, and a light output portion configured to output light from the internal space to the outside, the method comprising:
inputting light from the light input portion of the integrator to the internal space;
dispersing light of a first wavelength region in the light output from the light output portion and acquiring first spectrum data for a first exposure time by a first spectroscopic detector;
dispersing light of a second wavelength region partially overlapping with the first wavelength region in the light output from the light output portion and acquiring second spectrum data for a second exposure time by a second spectroscopic detector; and
analyzing the first spectrum data and the second spectrum data on the basis of the first exposure time and the second exposure time by an analysis unit.

9. The spectroscopic measurement method according to claim 8, wherein, by the analysis unit, a correction value calculated based on the first spectrum data and the second spectrum data in a common wavelength region which is a wavelength region in which the first wavelength region and the second wavelength region overlap is stored.

10. The spectroscopic measurement method according to claim 9, wherein, by the analysis unit, the number of photons in the common wavelength region is obtained on the basis of the first spectrum data, the number of photons in the common wavelength region is obtained on the basis of the second spectrum data, and the correction value is calculated on the basis of these numbers of photons.

11. The spectroscopic measurement method according to claim 9, wherein, by the analysis unit, an intensity integrated value in the common wavelength region is obtained on the basis of the first spectrum data, an intensity integrated value in the common wavelength region is obtained on the basis of the second spectrum data, and the correction value is calculated on the basis of these intensity integrated values.

12. The spectroscopic measurement method according to claim 9, wherein, by the analysis unit, at least one of the first spectrum data and the second spectrum data is corrected on the basis of the correction value, the first exposure time, and the second exposure time and a spectrum in an entire wavelength region including both the first wavelength region and the second wavelength region is obtained.

13. The spectroscopic measurement method according to claim 9, wherein when excitation light is input from the light input portion of the integrator to the internal space in a state where a measurement object which emits emission light by incidence of the excitation light is not disposed in the internal space, by the analysis unit, the number of photons in an excitation light wavelength region is obtained on the basis of the first spectrum data and the number of photons in an emission light wavelength region is obtained on the basis of the second spectrum data;

when the excitation light is input from the light input portion of the integrator to the internal space in a state where the measurement object is disposed in the internal space, by the analysis unit, the number of photons in the excitation light wavelength region is obtained on the basis of the first spectrum data and the number of photons in the emission light wavelength region is obtained on the basis of the second spectrum data; and based on these numbers of photons, the correction value, and the first exposure time and the second exposure time, by the analysis unit, luminous efficiency of the measurement object is evaluated.

14. The spectroscopic measurement method according to claim 8, wherein the second wavelength region is on a long-wavelength side compared to the first wavelength region, and the second exposure time is longer than the first exposure time.

* * * * *